(12) United States Patent
Warnke et al.

(10) Patent No.: US 8,547,331 B2
(45) Date of Patent: Oct. 1, 2013

(54) INTERACTIVE USER INTERFACES AND METHODS FOR VIEWING LINE TEMPERATURE PROFILES OF THERMAL IMAGES

(75) Inventors: Stefan H. Warnke, Santa Cruz, CA (US); James T. Pickett, Santa Cruz, CA (US)

(73) Assignee: Fluke Corporation, Everett, WA (US)

( * ) Notice: Subject to any disclaimer, the term of this patent is extended or adjusted under 35 U.S.C. 154(b) by 666 days.

(21) Appl. No.: 12/174,617

(22) Filed: Jul. 16, 2008

(65) Prior Publication Data

US 2010/0014746 A1 Jan. 21, 2010

(51) Int. Cl.
*G09G 5/08* (2006.01)
*G06T 11/20* (2006.01)
*G06K 9/00* (2006.01)

(52) U.S. Cl.
USPC .................... 345/157; 345/440; 382/141

(58) Field of Classification Search
None
See application file for complete search history.

(56) References Cited

U.S. PATENT DOCUMENTS

| 5,250,809 A * | 10/1993 | Nakata et al. ................ 250/330 |
| 5,637,871 A | 6/1997 | Piety et al. |
| 5,812,112 A | 9/1998 | Helfferich |
| 6,606,115 B1 | 8/2003 | Alicandro et al. |
| 2009/0227850 A1 * | 9/2009 | Rogers et al. ................ 600/306 |

* cited by examiner

*Primary Examiner* — Joni Richer
*Assistant Examiner* — Michelle Chin
(74) *Attorney, Agent, or Firm* — Fredrikson & Byron, P.A.

(57) ABSTRACT

An interactive graphical user interface includes a moveable pointer, which may be activated to select points of a computer-generated thermal image of an object, as the pointer is moved over a display of the image, so that line temperature profiles, which correspond to predetermined lines extending through the selected points, may be viewed, for example, on a line temperature profile chart of the interface, for each selected point as the pointer is moved. Each predetermined line extends between the corresponding selected point and another, predetermined, point of the image. The other predetermined point may either coincide with an origin of an x-axis or a y-axis of an orthogonal coordinate system, in which the image is aligned, or may be any other point of the thermal image, for example, one that is pre-selected by a user, with the moveable pointer.

21 Claims, 8 Drawing Sheets

INTERACTIVE USER INTERFACES AND METHODS FOR VIEWING LINE TEMPERATURE PROFILES OF THERMAL IMAGES

TECHNICAL FIELD

The present invention pertains to interactive user interfaces and methods used for analyzing thermal images, and more particularly, to those employed for viewing line temperature profiles.

BACKGROUND

Thermal images of electrical devices, mechanical devices and structures can be useful for analyzing the performance thereof, both during design and development, for example, for design optimization purposes, and during operational service, for example, for inspection and maintenance purposes. These thermal images may be captured, displayed, stored and transferred to a computer workstation by an infrared (IR) camera, according to methods known to those skilled in the art. A particular example of such a camera, is the Fluke Ti 20 Thermal Imager.

A displayed thermal image of an object, or scene, is composed of corrected digital image data that has been mapped and scaled to an array of pixels, wherein a color, or a gray-scale value, of each pixel corresponds to a detected temperature, or temperature range, of the corresponding portion of the object. Although such an image can indicate to a viewer, the general location of hot spots, and can give an idea of temperature gradients over the object, more focused and quantitative methods have been proposed for viewing select subsets of data, for example, line temperature profiles, taken from the large quantity of temperature data that makes up each thermal image. Even so there is still a need for more efficient and selective methods for viewing these select subsets of data, along with the interactive user interfaces to enable these methods.

BRIEF DESCRIPTION OF THE DRAWINGS

The following drawings are illustrative of particular embodiments of the invention, and are not intended to limit the scope of the invention. The drawings are not to scale (unless so stated) and are intended for use in conjunction with the explanations in the following detailed description. Due to the limitations imposed on patent application Figures, with respect to color, the image of FIG. 2, although originally coded with color values from the spectrum of visible light, is shown in a grayscale format, which is a function of grayscale reproduction. Furthermore, it should be noted that a line drawing format for similarly coded thermal images is used in FIGS. 3, 4A-D and 5, as opposed to the grayscale format, in order to enhance clarity in the illustration of interactive user interface features. Embodiments of the disclosure will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments. Utilizing the teaching provided herein, those skilled in the art will recognize that many of the examples have suitable alternatives that can be utilized.

Figure 1:
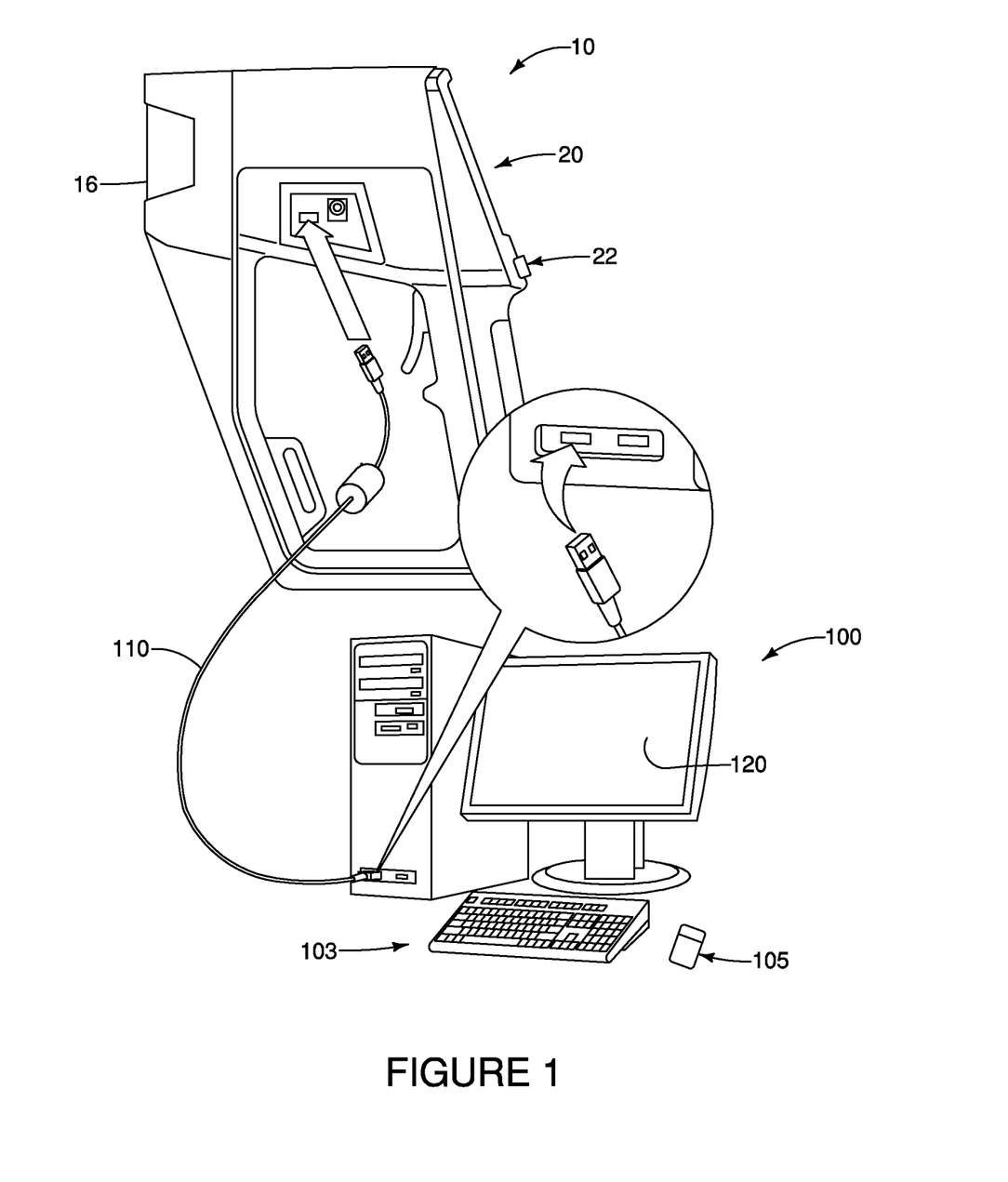
FIG. 1 is a schematic of an exemplary thermal imaging and analysis system including an IR camera and a workstation, either of which may employ embodiments of the present invention.

FIG. 1 is a schematic of an exemplary thermal imaging and analysis system including an IR camera 10 and a workstation 100, for example, a personal computer, on which software for manipulating data transferred from camera 10 is loaded. FIG. 1 illustrates camera 10 including a focus ring 16 for focusing an IR lens (not shown) of camera 10; those skilled in the art will appreciate that camera 10 further includes an IR sensor assembly, for example, a microbolometer focal plan array, aligned with the IR lens, which is focused with ring 16, to receive IR radiation data from an object, or scene, of interest. Electronics included in camera 10 convert the raw IR radiation to digital image data, and then correct, map and scale the digital image data for display, according to methods known in the art. FIG. 1 further illustrates camera 10 including a display 20, and workstation 100, which also includes a display 120, both of which are adapted to display a thermal image of the object, like that shown in FIG. 2. Although FIG. 1 illustrates a data transfer cord 110 for coupling camera 10 to workstation 100, in order to transfer data therebetween, it should be understood that alternative means, such as wireless communication and/or a plug-in memory card may be employed to transfer the data.

Figure 2:
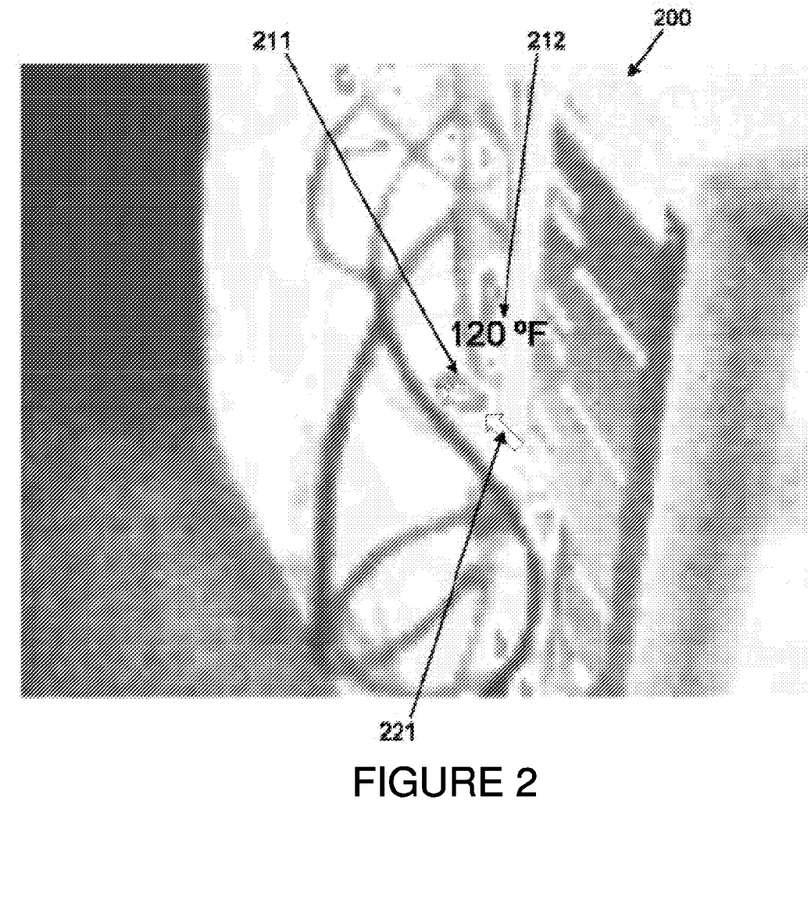
FIG. 2 is an exemplary thermal image, which may be displayed by the camera and/or the workstation of FIG. 1.

FIG. 2 is an exemplary thermal image 200, wherein a gray-scale value, of each pixel corresponds to a detected temperature, or temperature range, of the corresponding portion of the object. FIG. 2 illustrates a pointer 221, which is moveable over thermal image 200, to select points on image 200 and thereby gather temperature information. FIG. 2 further illustrates a marker 211 and a corresponding temperature reading 212, which are overlaid on image 200. According to FIG. 2, pointer 221 was previously moved over the point coinciding with marker 211 in order to select the point. With reference back to FIG. 1, once the data defining thermal image 200 is transferred to workstation 100, either a keyboard 103 thereof, or a mouse 105 thereof, may be used to move pointer 221 over image 200, for example, when image 200 is displayed on display 221. According to some embodiments, one or more buttons 22 of camera 10 may be used to move pointer 221 over thermal image 200, for example, when image 200 is displayed on display 20. Methods which may be employed to move pointer 221 (or any of the other pointers described herein, below), with any of the aforementioned devices 22, 103, 105, are known to those skilled in the art; and each of the aforementioned devices 22, 103, 105 may further include an element or elements that further allow the user to select with pointer 221 (or any of the other pointers described herein, below), for example, a button, which when depressed, activates pointer 221 for selection.

Figure 3:
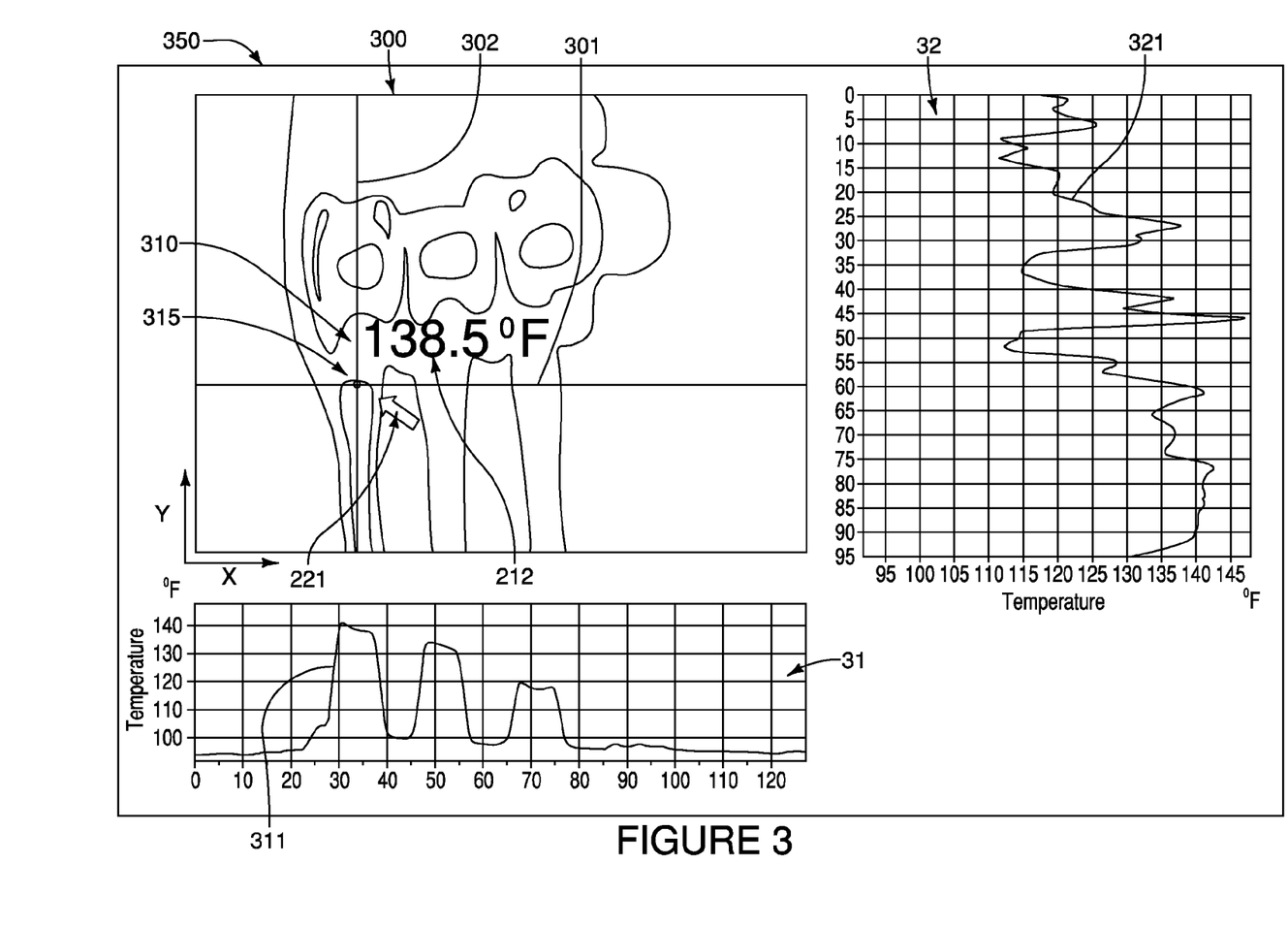
FIG. 3 is an exemplary display of a thermal image including items of a user interface for viewing line temperature profiles.

Thus, with reference to FIG. 2, it may be appreciated that pointer 221 may be sequentially moved and then activated to select a series of points on image 200, at which points temperature readings are desired, thereby collecting a corresponding series of temperature readings that may help to quantify one or more temperature gradients across portions of the object. Turning now to FIG. 3, a display 350 is shown wherein pointer 221 is enabled to select a plurality of points at a time, rather than just one at a time, on a thermal image 300.

According to FIG. 3, pointer 221 has selected a point that is associated with a pair of orthogonal predetermined lines, each of which extends through the selected point; the selected point is marked by a cross-point 315 of a marker 310, and the predetermined lines by lines 301, 302 of marker 310. FIG. 3 further illustrates thermal image 300 being aligned within an orthogonal x-y coordinate system, and the user interface of display 350 including a first chart 31 (temperature vs. x) and a second chart 32 (y vs. temperature), in which line temperature profiles 311 and 321, respectively are plotted. Line temperature profile 311 corresponds to the predetermined line marked by line 301 of marker 310, and line temperature profile 321 corresponds to the predetermined line marked by line 302 of marker 310. With reference to FIG. 3, it may be appreciated that the predetermined line marked by line 301 of marker 310 extends from an origin of, and parallel to, the x-axis of the coordinate system in which image 300 is aligned, while the predetermined line marked by line 302 of marker 310 extends from an origin of, and parallel to, the y-axis of the coordinate system.

According to prior methods, associated with the user interface of display 350, pointer 221 is activated to select one or more additional points on thermal image 300 after being moved to, and coming to a stop at, each additional point; and, when each of the additional points is selected by pointer 221, charts 31 and 32 are updated to correspond with the associated new predetermined lines. Thus, if the user is interested in viewing a line temperature profile at a number of different positions in image 300, the user would need to activate pointer 221 multiple times, after moving the pointer in multiple discrete steps. In contrast, according to some methods of the present invention, an interactive user interface is configured to allow the user to activate a pointer once, and then to move the activated pointer over the thermal image while viewing at least one dynamically updated line temperature profile chart that corresponds with each point passed over by the pointer as the activated pointer is being moved. Such a user interface, and the associated method, will be described in conjunction with FIGS. 4A-D.

Figure 4A:
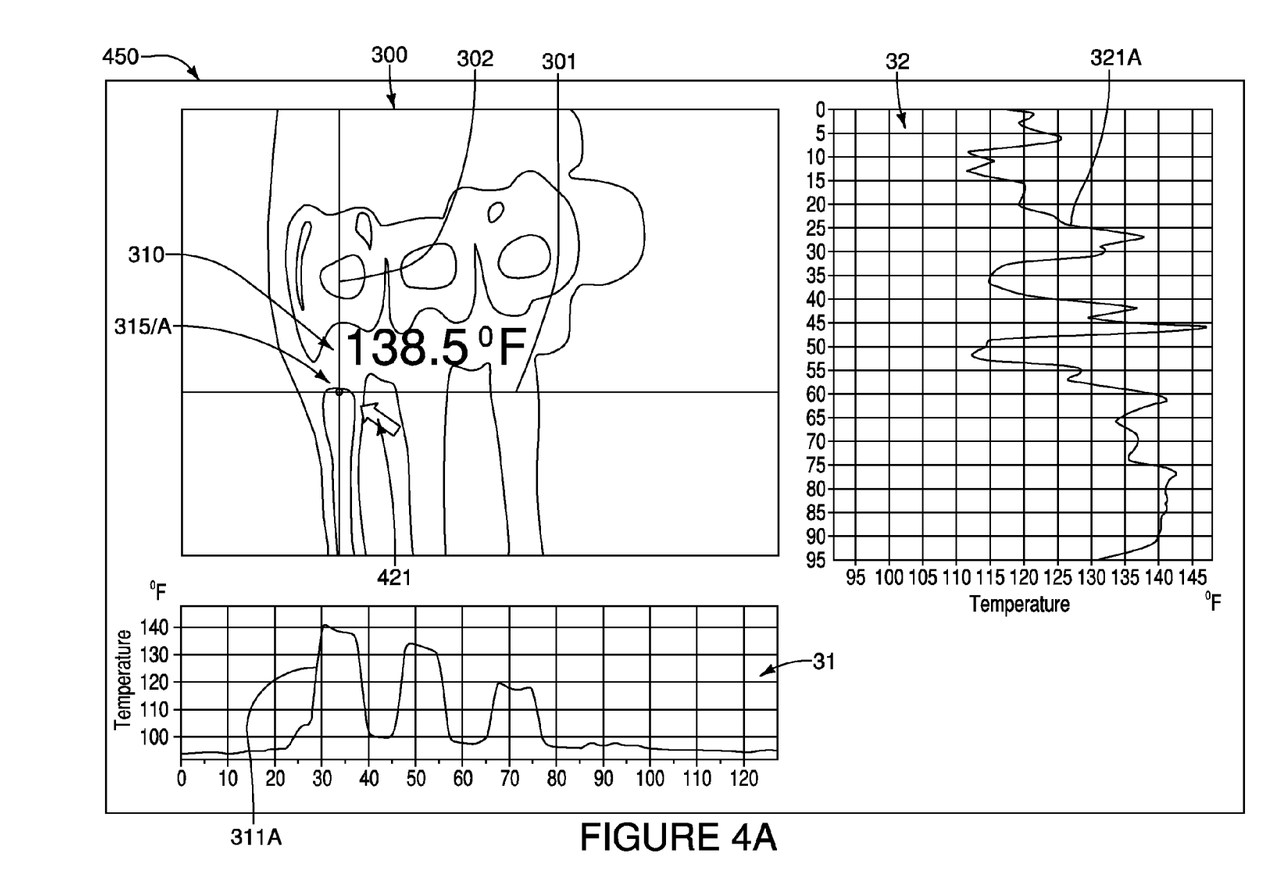
FIGS. 4A-D are a sequential presentations of a display that includes the thermal image of FIG. 3, according to some embodiments of the present invention.
Figure 4B:
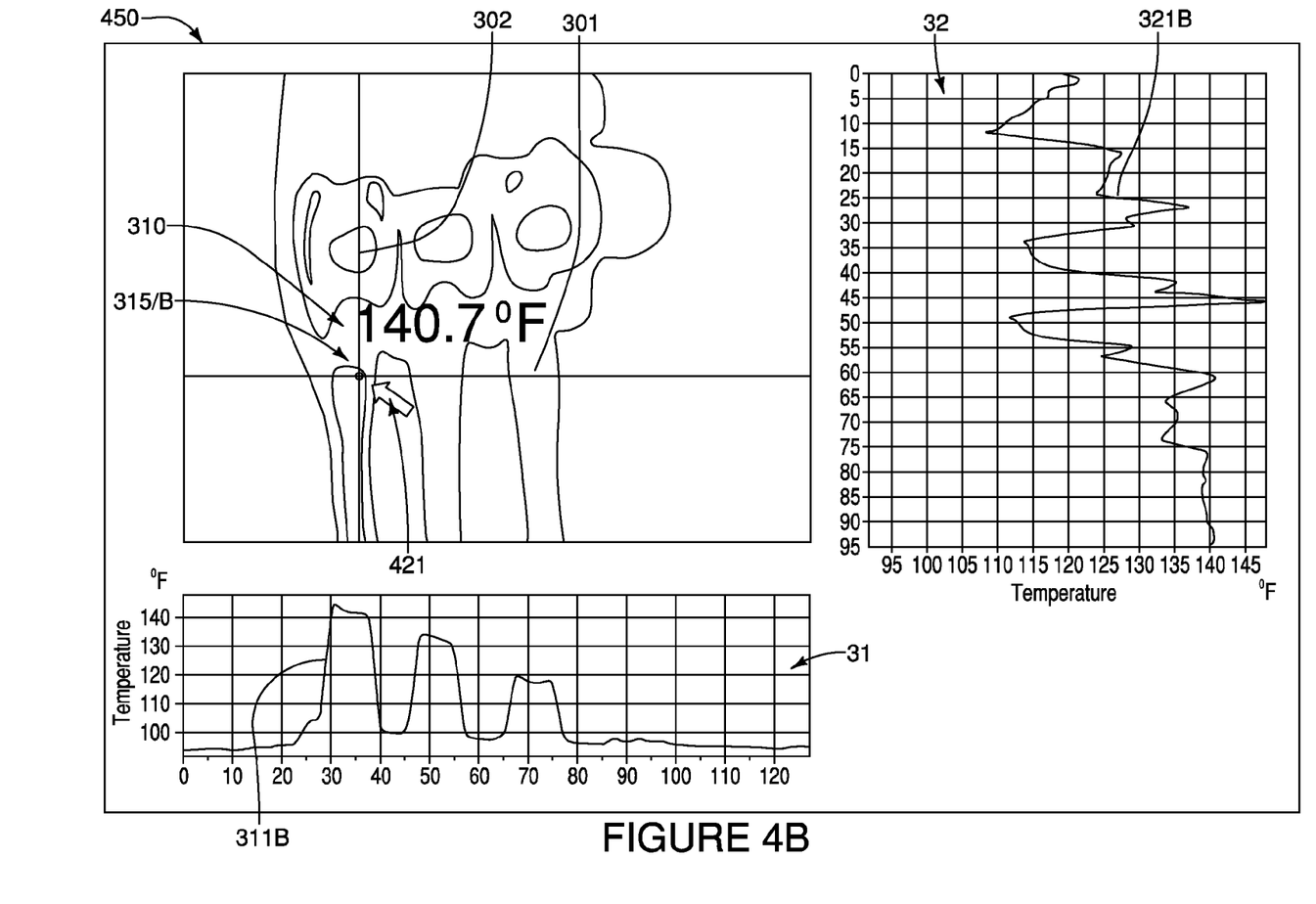
Figure 4C:
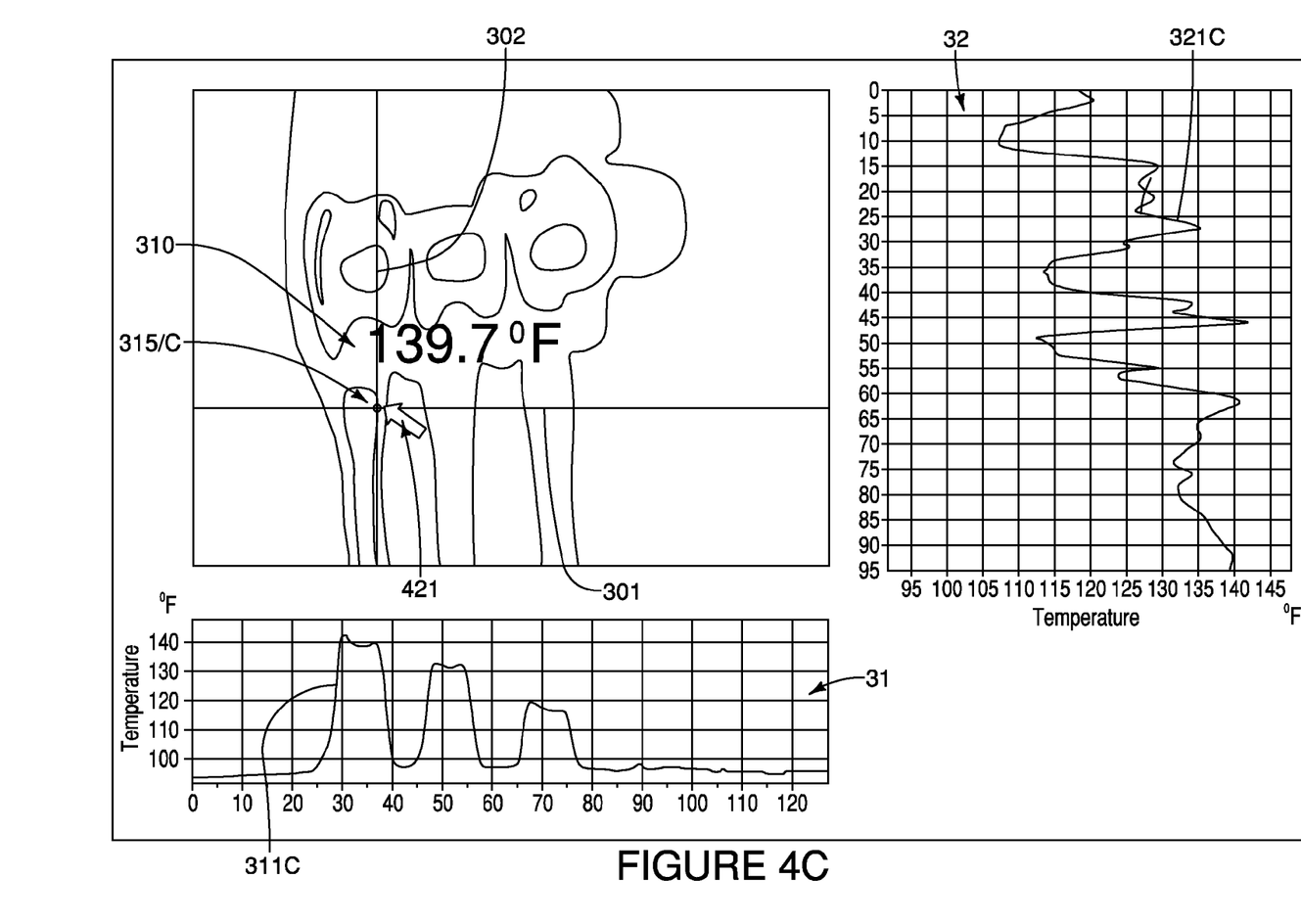
Figure 4D:
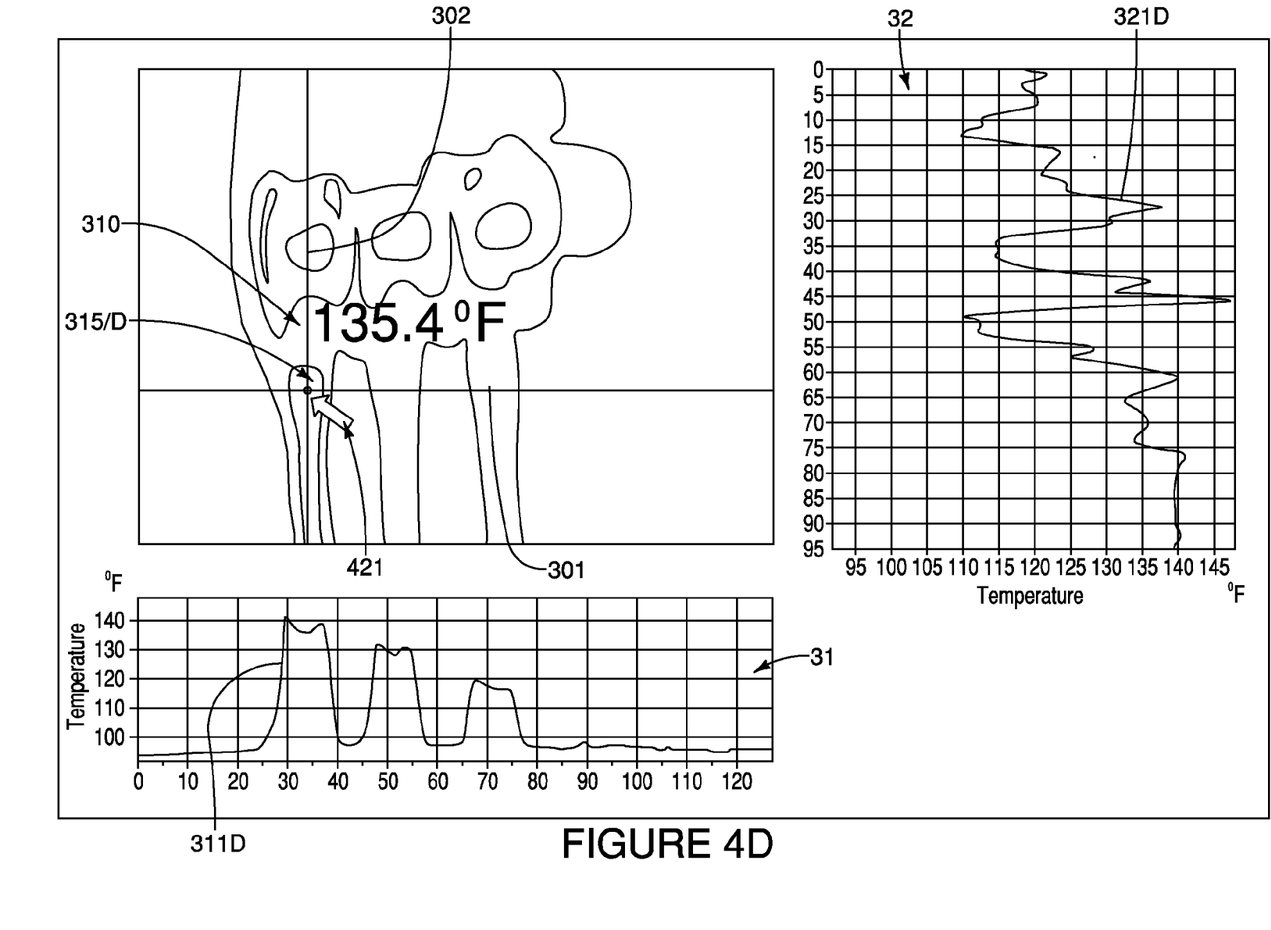

FIGS. 4A-D are sequential presentations of a display 450 that includes thermal image 300 over which a pointer 421 is being moved. It should be noted that FIGS. 4A-D are intended to reflect the movement of pointer 421, without stopping, after pointer 421 is initially activated at a first point A, which is marked by cross-point 315 of marker 310, in FIG. 4A. FIGS. 4A-D illustrate activated pointer 421 moving from first point A to a second point B, which is marked by cross-point 315, and from second point B to a third point C, which is marked by cross-point 315, and from third point C to a fourth point D, which is marked by cross-point 315. As activated pointer 421 is moved from first point A, at which line temperature profiles 311A, 321A are shown in charts 31 and 32, respectively, charts 31, 32 are dynamically updated to show line temperature profiles 311B, 321B (corresponding to second point B; FIG. 4B), and then 311C, 321C (corresponding to third point C; FIG. 4C), and then 311D, 321D (corresponding to fourth point D; FIG. 4D). The resolution of the movement of activated pointer 421 may at least match that of the pixel resolution of displayed thermal image 300, such that the rate at which the line temperature profiles are updated corresponds to speed at which pointer 421 is moved and the pixel resolution.

Although FIGS. 4A-D show marker 310 including orthogonal pairs of lines 301, 302, which mark the predetermined lines along which the corresponding line temperature profiles are plotted, according to some other embodiments, marker 310 need only include cross-point 315. Furthermore, according to some alternate embodiments, rather than showing line temperature profiles for each of the orthogonal pair of predetermined lines, only single line temperature profiles may be shown for a single predetermined line, either parallel to the x-axis or parallel to the y-axis, thereby eliminating one of charts 31, 32 from the user interface of display 450. According to yet further alternate embodiments, an interactive user interface enables viewing of temperature profiles, which correspond to predetermined lines that extend at an angle with respect to both the x-axis and y-axis of the coordinate system, in which a thermal image is aligned. Such a user interface will be described in conjunction with FIG. 5.

Figure 5:
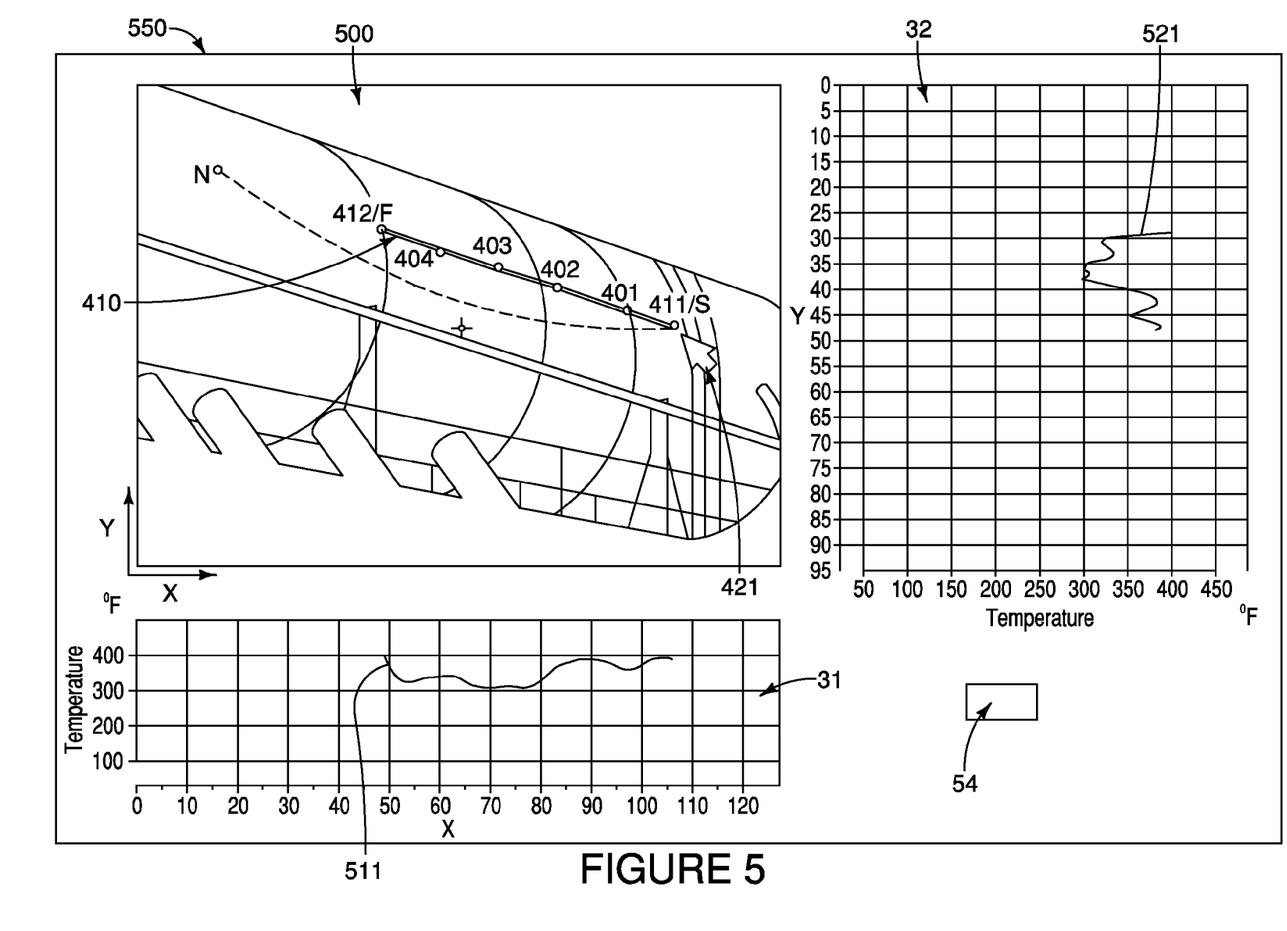
FIG. 5 is an exemplary display of a thermal image, including items of a user interface, according to some alternate embodiments of the present invention.

FIG. 5 is a display 550 of a thermal image 500, wherein pointer 421 may be moved by the user to generate a predetermined line that extends over any desired length and at any angle within image 500. FIG. 5 illustrates a line marker 410, which coincides with the predetermined line that extends between a first point S, which is marked by a first end point 411 of line marker 410, and a second, fixed point F, which is marked by a second end point 412 of line marker 410. According to the illustrated embodiment, first point S has been selected by pointer 421 in order to generate the predetermined line extending thereto from second, fixed point F, so that a line temperature profile, which corresponds to the predetermined line, may be viewed. A dashed line in FIG. 5 indicates a path over which pointer 421 may be moved, by the user, to generate a new predetermined line that would extend from second, fixed point F to a newly selected point N.

According to some preferred embodiments, pointer 421 may be activated and moved along the dashed line so that one or more line temperature profiles, which correspond to new lines that extend from fixed point F to each new point that pointer 421 passes through may be dynamically plotted, as pointer 421 is moved, for example, in a similar fashion to that previously described in conjunction with FIGS. 4A-D. It should be noted first point S, rather than second point F, may be fixed, while pointer 421 is used to move second point F in order to generate a new predetermined line. Furthermore, the user may have used pointer 421 to initially select second point F, prior to selecting first point S.

FIG. 5 further illustrates the interface of display 550 including charts 31 and 32 on which line temperature profiles 511 and 521, respectively, are plotted, according to some embodiments; profile 511 includes x-coordinates of each point F, S and 401-404, of the user-generated predetermined line, plotted versus temperature, while profile 521 includes y-coordinates of the aforementioned points plotted versus temperature. Thus the line temperature profiles 511, 521 are projections of the user-generated predetermined line onto the x- and y-axes, respectively. According to some alternate embodiments, display 550 includes a single chart, for example, oriented along marker 410, to display a plot of temperature versus position along the predetermined line coinciding with marker 410. With reference to FIG. 5, which is an exemplary thermal image of a cement kiln, it may be appreciated that user-generated predetermined lines are useful for selecting paths of interest along an element or component, for example, the vessel of the kiln, which do not happened to be aligned with one of the x- or y-axis of the orthogonal x-y coordinate system of the image.

According to yet further embodiments, a plurality of end-connected predetermined lines, which extend at any angle with respect to one another, may be selected by a user, so that a plurality of line temperature profiles, corresponding to the plurality of predetermined lines, may be viewed simultaneously. The plurality of end-connected predetermined lines may comprise, for example, a 'splined' curve or a polygon.

With further reference to FIG. 5, a toggle-type switch 54 is shown included in the interactive interface of display 550. According to some embodiments, the user may select switch 54, with pointer 421, to switch back and forth between the type of predetermined lines, for line temperature profiles, which is described above, for display 550, and the type of predetermined lines, for line temperature profiles, which was previously described in conjunction with FIGS. 4A-D.

In the foregoing detailed description, the invention has been described with reference to specific embodiments. However, it may be appreciated that various modifications and changes can be made without departing from the scope of the invention as set forth in the appended claims.

We claim:

1. A method for displaying, on an interactive computer display, multiple line temperature profiles of a computer-generated thermal image of an object, the thermal image being presented on the computer display, the method comprising:
   activating a moveable pointer;
   selecting, with the movable pointer, a first point of the thermal image from an array of points defining the thermal image;
   displaying on the computer display a first line temperature profile corresponding to a first predetermined line of the thermal image that extends through the first point and comprises temperature information for a plurality of points along the line;
   after displaying the first line temperature profile, moving the activated pointer from the first point of the thermal image to a second point of the thermal image, and from the second point to a third point of the thermal image, without stopping at the second point; and
   displaying on the computer display a second line temperature profile corresponding to a second predetermined line of the thermal image, that extends through the second point, and then a third line temperature profile corresponding to a third predetermined line of the thermal image, that extends through the third point;
   wherein displaying the first, second and third line temperature profiles occurs in sequence as the activated pointer is being moved.

2. The method of claim 1, wherein the first, second and third line temperature profiles are viewed on a chart that is presented alongside the thermal image, on the computer display.

3. The method of claim 1, further comprising:
   displaying a fourth line temperature profile corresponding to a fourth predetermined line, that extends through the first point, a fifth line temperature profile corresponding to a fifth predetermined line, that extends through the second point, and a sixth line temperature profile corresponding to a sixth predetermined line, that extends through the third point;
   wherein displaying the fourth line temperature profile occurs simultaneously with displaying the first line temperature profile;
   displaying the fifth line temperature profile occurs simultaneously with displaying the second line temperature profile; and
   displaying the sixth line temperature profile occurs simultaneously with displaying the third line temperature profile.

4. The method of claim 3, wherein the fourth predetermined line extends orthogonal to the first predetermined line, the fifth predetermined line extends orthogonal to the second predetermined line, and the sixth predetermined line extends orthogonal to the third predetermined line.

5. The method of claim 3, wherein:
   the thermal image is aligned within an x-y orthogonal image coordinate system;
   the first, second and third predetermined lines extend from an origin of, and parallel to, an x-axis of the image coordinate system, the first, second and third lines being offset from one another along a y-axis of the image coordinate system;
   the first, second and third line temperature profiles are viewed on a first chart that is presented alongside the thermal image, on the computer display, at a first location, the first chart comprising an x-axis and a temperature axis extending orthogonal to the x-axis of the first chart, the x-axis of the first chart extending parallel to the x-axis of the image coordinate system and having an origin aligned with the origin thereof;
   the fourth, fifth and sixth predetermined lines extend from an origin of, and parallel to, the y-axis of the image coordinate system, the fourth, fifth and sixth lines being offset from one another along the x-axis of the image coordinate system; and
   the fourth, fifth and sixth line temperature profiles are viewed on a second chart that is presented alongside the thermal image, on the computer display, at a second location, the second chart comprising a y-axis and a temperature axis extending orthogonal to the y-axis of the second chart, the y-axis of the second chart extending parallel to the y-axis of the image coordinate system and having an origin aligned with the origin thereof.

6. The method of claim 1, wherein the first predetermined line extends straight from a fixed point of the thermal image to the first point of the image, the second predetermined line extends straight from the fixed point to the second point of the thermal image, and the third predetermined line extends from the fixed point to the third point of the thermal image.

7. The method of claim 6, further comprising activating the pointer of the display to select the fixed point prior to activating the pointer to select the first point and moving the activated pointer from the first point to the second point, and from the second point to the third point.

8. A method for displaying, on an interactive computer display, multiple line temperature profiles of a thermal image of an object, the thermal image being presented on the computer display, the method comprising: activating a movable pointer to select a first point of the thermal image, the first point being located with respect to a second point on the image, at which a marker of the display is located, in order to generate a first line between the first and second points; displaying a first line temperature profile corresponding to the first line; after displaying the first line temperature profile, moving the activated pointer to a third point on the thermal image while the marker remains located at the second point in order to generate a second line between the second and third points; displaying a second line temperature profile corresponding to the second line; and after displaying the second line temperature profile, moving the activated pointer to a fourth point on the thermal image while the marker remains located at the second point, in order to generate a third line between the second and fourth points, and displaying a third line temperature profile corresponding to the third line.

9. The method of claim 8, wherein:

the thermal image is aligned within an x-y orthogonal coordinate system; and each of the first, second and third line temperature profiles are presented along a projection of the first, second and third lines, respectively, onto one of an x-axis and a y-axis of the coordinate system.

10. The method of claim 8, further comprising selecting the second point of the thermal image with the pointer, prior to selecting the first point.

11. A non-transitory computer readable medium containing executable instructions causing one or more processors to perform a method providing an interactive graphical user interface for displaying line temperature profiles of a computer-generated thermal image of an object, in conjunction with the thermal image of the object, on a display, the user interface comprising:

a pointer being movable over the displayed thermal image to select points of the thermal image from an array of points defining the image, the points being selectable when the pointer is activated, and as the pointer is being moved; and a line temperature profile chart, which is dynamically updated as the activated pointer is being moved, in order to show a line temperature profile corresponding to each selected point;

wherein each line temperature profile corresponds to a predetermined line extending through the corresponding selected point;

and wherein the method comprises:

receiving a first selected point, selected by the movable pointer, displaying, on the display, a first line temperature profile corresponding to a predetermined line extending through the first selected point;

receiving a second selected point after the displaying the first line temperature profile, the second selected point selected by the moveable pointer; and displaying, on the display, a second line temperature profile corresponding to a predetermined line extending through the second selected point.

12. The computer readable medium of claim 11, further comprising:

a marker overlaid on the display;

wherein the marker moves with the activated pointer and thereby coincides with each selected point as the pointer selects each point.

13. The computer readable medium of claim 12, wherein the marker comprises a line coinciding with the predetermined line extending through each selected point.

14. The computer readable medium of claim 11, wherein:

the displayed thermal image is aligned within an x-y orthogonal image coordinate system; and each predetermined line extends from an origin of, and parallel to, one of an x-axis of the image coordinate system and a y-axis of the image coordinate system.

15. The computer readable medium of claim 14, further comprising:

a marker overlaid on the display;

wherein the marker moves with the activated pointer and comprises a line coinciding with the predetermined line extending through each selected point.

16. The computer readable medium of claim 11, wherein each predetermined line extends straight from a fixed point to each selected point as the pointer selects each point.

17. The computer readable medium of claim 16, wherein the fixed point is selectable with the pointer.

18. The computer readable medium of claim 16, further comprising:

a marker overlaid on the display;

wherein the marker moves with the activated pointer and comprises a line coinciding with the predetermined line extending through each selected point.

19. The computer readable medium of claim 18, wherein the marker further comprises a first end point of the line, coinciding with each selected point, and a second end point of the line, coinciding with the fixed point.

20. The computer readable medium of claim 11, further comprising:

a toggle-type switch;

wherein the pointer, when positioned over the switch and activated, selects between at least two types of predetermined lines for the line temperature profiles;

wherein a first type of predetermined line extends from an origin of, and parallel to, one of an x-axis and a y-axis of an orthogonal coordinate system in which the displayed thermal image is aligned; and a second type of predetermined line extends from a fixed point straight to each selected point, as the pointer selects each point.

21. The computer readable medium of claim 20, wherein the fixed point is selectable with the pointer.

* * * * *